United States Patent
Bersin

(10) Patent No.: US 6,190,356 B1
(45) Date of Patent: *Feb. 20, 2001

(54) HELICAL SPIRAL BALLOON CATHETER

(76) Inventor: Robert M. Bersin, 2005 Cortelyou Rd., Charlotte, NC (US) 28211

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/175,773

(22) Filed: Oct. 20, 1998

Related U.S. Application Data

(60) Provisional application No. 60/062,532, filed on Oct. 20, 1997.

(51) Int. Cl.[7] .................................................. A61M 29/00
(52) U.S. Cl. ............................. 604/101.01; 604/103.07; 604/509
(58) Field of Search ............................. 604/96, 101, 103, 604/509, 508, 96.01, 101.01, 101.05, 103.01, 103.06, 103.07

(56) References Cited

U.S. PATENT DOCUMENTS

| | | | |
|---|---|---|---|
| 5,383,856 | * | 1/1995 | Bersin ................................. 604/101 |
| 5,395,333 | * | 3/1995 | Brill .................................... 604/101 |
| 5,505,702 | * | 4/1996 | Arney .................................. 604/101 |
| 5,759,172 | * | 6/1998 | Weber et al. ........................ 604/96 |
| 5,797,948 | * | 8/1998 | Dunham .............................. 604/101 |
| 5,853,389 | * | 12/1998 | Hijlkema ............................. 604/96 |

* cited by examiner

*Primary Examiner*—Anhtuan T. Nguyen
(74) *Attorney, Agent, or Firm*—Miles & Stockbridge P.C.; John C. Kerins

(57) ABSTRACT

A balloon catheter device designed to be especially well suited for use in providing medical treatment within a blood vessel, and a method for conducting such medical treatment are provided, wherein the balloon catheter has a central support tube or lumen, and has, near a distal end of the catheter, a plurality of inflatable balloon elements extending along the catheter in helical patterns, with the balloon elements spaced equidistantly around the central support tube. The catheter thus provides the ability to apply pressure, by way of the inflated balloon elements, to center the central support tube in the blood vessel, while at the same time preserving blood flow in the blood vessel past the catheter as well as in side branch blood vessels extending from the blood vessel under repair.

12 Claims, 4 Drawing Sheets

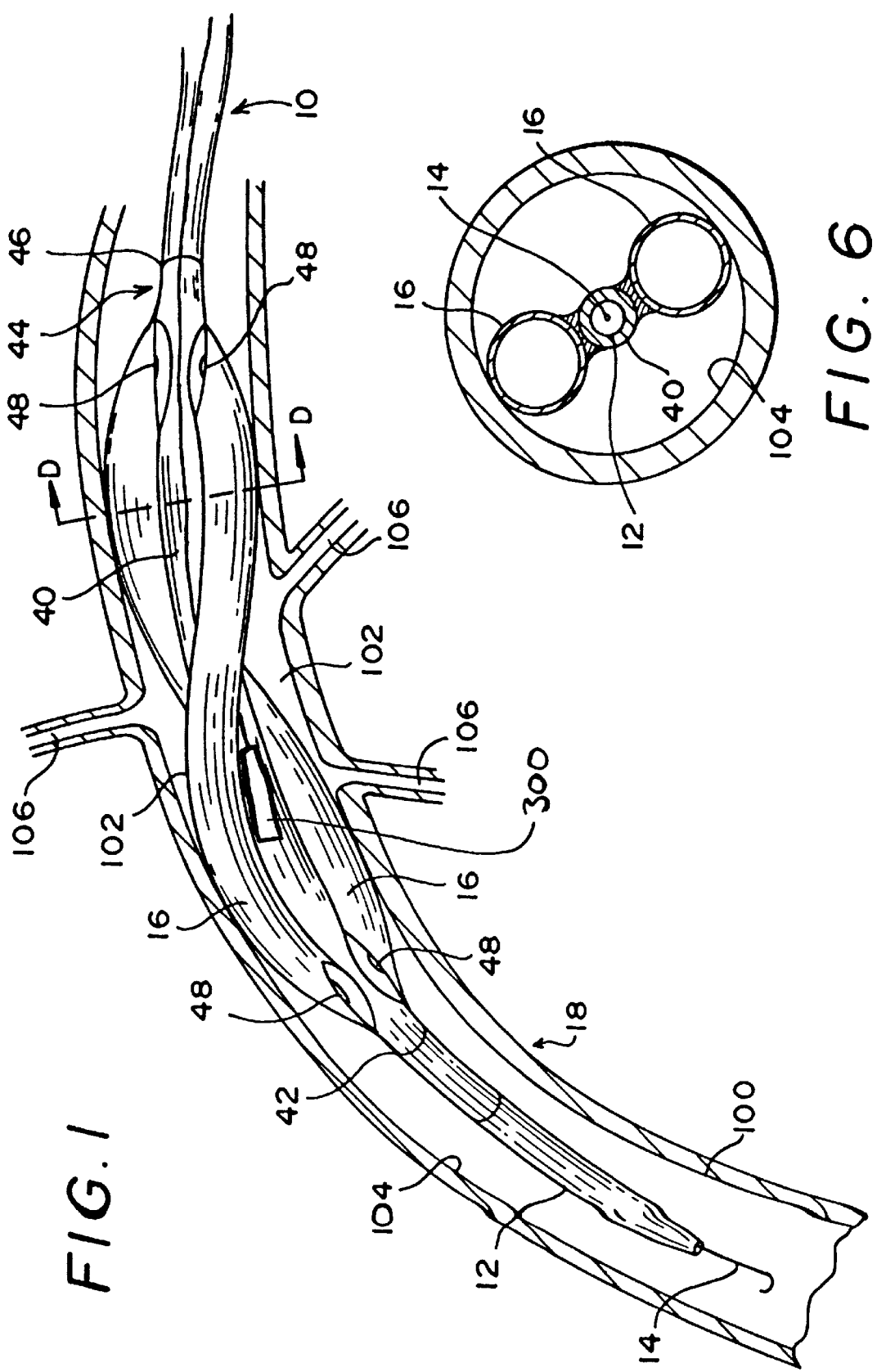

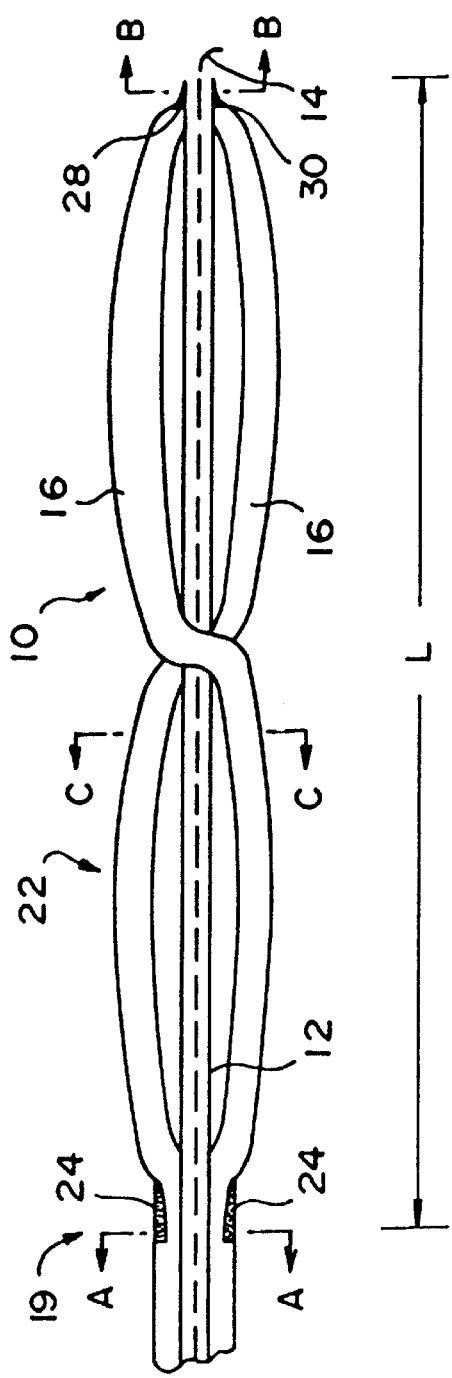
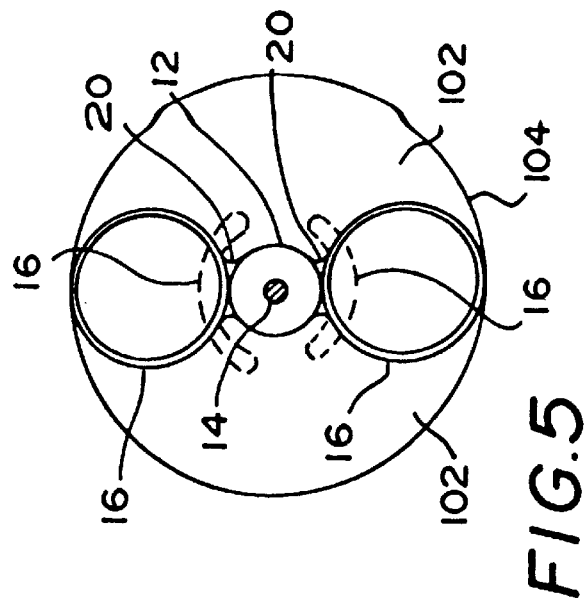
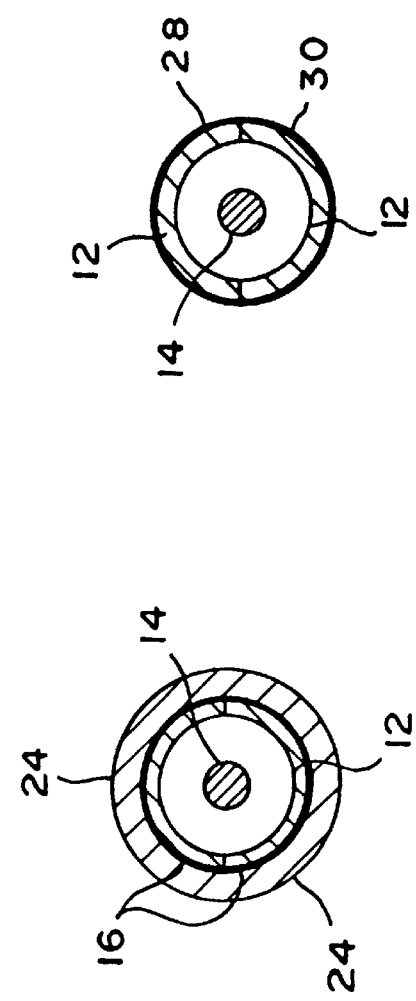

HELICAL SPIRAL BALLOON CATHETER

This application contains subject matter disclosed in, and claims the benefit of the filing date of, U.S. Provisional Patent Application Serial No. 60/062,532, filed Oct. 20, 1997.

BACKGROUND OF THE INVENTION

1. Field of the Invention

The present invention relates to balloon catheters, and more particularly to catheters for use in centering a central support tube in a blood vessel for use in a medical treatment process.

2. Description of Related Art

Several designs of dilatation balloon catheters have been proposed in the prior art, examples of which can be seen in U.S. Pat. No. 5,160,321; U.S. Pat. No. 5,090,958; U.S. Pat. No. 4,787,388; and U.S. Pat. No. 4,581,017. Each of those balloon dilatation catheters was designed for the purpose of administering treatments to physically widen constricted blood flow passages. The term stenosis is used in this regard to refer to a region of a blood vessel which has been narrowed or constricted to such a degree that blood flow is restricted. In severe instances, treatment of the stenosis is required. Treatment of coronary blood vessels by use of the aforenoted prior art dilatation balloon catheters is referred to in the art as percutaneous transluminal coronary angioplasty (PTCA), which procedure is described in various forms in the patents identified above. The term "dilatation catheter", as used herein, will refer to the type of catheter which is principally designed for use in widening constricted blood flow passages, as is done in the PTCA procedure.

One problem associated with PTCA which has been recognized in, for example, U.S. Pat. No. 4,581,017, issued to Sahota, and U.S. Pat. No. 4,787,388, issued to Hofmann, is that, in performing the PTCA procedure, blood flow cannot be completely occluded for extended periods of time, measured in terms of well under one minute, due to the increased probability that serious damage to the patient's heart or other downstream vessels or organs will occur. The Sahota patent presents two approaches to solving this problem, a first of which is to provide a balloon catheter which, even though the inflated balloon completely occludes the blood vessel, i.e., the balloon inflates into contact with the blood vessel around the entire circumference of the blood vessel, blood is permitted to flow from a proximal side of the balloon to the distal (downstream) side of the balloon through a central lumen. The second solution proposed by Sahota, which appears to be conceptually the same as the Hofmann solution, is to design the balloon such that, when the balloon is expanded or inflated, it will not completely occlude blood flow, but which will, at the same time, provide sufficient area of balloon contact around the circumference of the blood vessel such that the tissue or other matter creating the constriction in the blood vessel can be compressed against the vessel wall in an effective manner. These designs purport to permit a longer dilatation period to be used when performing the PTCA procedure.

A further balloon catheter design of which the present inventor is aware is disclosed in U.S. Pat. No. 4,762,130, issued to Fogarty et al. This catheter was not designed as a dilatation catheter for use in performing the PTCA procedure, but instead was developed for use in removing blood clots from blood vessels, and also for use as a diagnostic tool carrying diagnostic equipment in a lumen or lumens associated with the catheter. The corkscrew shape of the balloon on this catheter was adopted specifically to avoid the application of diametrically opposed forces on the wall of the blood vessel, so as to minimize the possibility of abrasions and/or perforations occurring in the vessel wall. As such, this balloon catheter would be particularly unsuitable for use in performing the PTCA procedure or for other procedures requiring some amount of diametrically opposed force or other opposing forces to be applied.

It has previously been noted that dissection of the blood vessel is a potential problem in performing the PTCA procedure, and one or more of the aforenoted patents directed to a dilatation catheter discuss procedural steps which attempt to minimize the possibility that dissection will occur. None of the above-noted dilatation catheter patents discusses providing a balloon-type catheter having a balloon configuration which is especially well-suited for use in repairing or tacking such dissections.

It is a principal object of the present invention to provide a balloon-type catheter having features making it especially well-suited for use in processes that call for medical treatment to be administered from inside a blood vessel, and that require the treatment agent to be centered in the blood vessel to the greatest degree practicable.

It is a further principal object of the present invention to provide a balloon-type catheter in which a plurality of balloons are configured in a helical or spiral pattern extending around a central support tube or lumen, whereby a medical treatment can be administered from inside the blood vessel while preserving blood flow down the main trunk or blood vessel, and also in side branches extending from the main trunk.

SUMMARY OF THE INVENTION

Since the issuance of U.S. Pat. No. 5,383,856, to the instant inventor, it has further been determined that a balloon catheter having a central support tube and a plurality of balloon elements extending helically around the central tube can advantageously be used in medical procedures in which the treatment or therapy is to be administered by holding a therapeutic agent in a central portion of a blood vessel for a predetermined period of time. The catheter device for administering therapy from within a blood vessel preferably will have diametrically opposed forces, or forces applied at substantially equal distances around the periphery of a cross-section of the blood vessel, thereby keeping the central support tube substantially centered in the blood vessel, and will, at the same time, permit blood to flow past the balloons, even when inflated.

One type of therapy that is currently being explored is a radiation therapy in which the object is to center, in an artery or other blood vessel, a radium implant, for periods of time on the order of fifteen minutes. For such radiation treatment, it is important to position the radium implant as closely as possible to the center of the artery. It is also important that blood flow past the implant be maintained, so as to not further disrupt normal body functions.

The balloon catheter of the present invention provides a configuration which permits continued perfusion along the main blood vessel in which the medical treatment is being performed, and provides improved protection of flow to side branch blood vessels extending from the main blood vessel, all while the balloons of the catheter are expanded or inflated and are performing their function of centering the central support tube. Both of these features have been determined to be of substantial importance in a balloon catheter whose principal purpose is to permit the use of medical treatments which last for an extended duration, such as on the order of at least several minutes, and in which it is desired or required to keep the treatment agent equally spaced from the side wall of the blood vessel.

In one or more of the above-noted patents disclosing dilatation catheter devices, the desirability of retaining blood flow down the main blood vessel being treated was recognized, even for relatively short-term occlusion of the blood vessel by the catheter. However, none of those patents discuss the importance of protecting (by preserving) blood flow into said branch vessels. This is likely due to the fact that the dilatation balloon catheters, even when inflated for what would be considered to be extended periods of time in the PTCA procedure, would be inflated and blocking off most, if not all, side branch flow for a time measured in terms of seconds, or at most in terms of a minute or two. In contrast, the medical treatment from within a blood vessel may require on the order of fifteen minutes, and possibly, as techniques improve, on the order of one to several hours or up to approximately one day or more. These medical treatments generally cannot afford to have the balloons moved or deflated to allow blood flow, and therefore the continuous inflation capability provided by the instant invention is important.

Preserving the blood flow to the side branches, which is not as critical over lengths of time on the order of several seconds to several minutes, becomes a very important consideration when longer time periods are involved, and is thus a very important consideration in the design of the balloon catheter of the present invention.

BRIEF DESCRIPTION OF THE DRAWINGS

These and other features of the present invention and the attendant advantages will be readily apparent to those having ordinary skill in the art and the invention will be more easily understood from the following detailed description of the preferred embodiments of the present invention taken in conjunction with the accompanying drawings, wherein like reference characters represent like parts throughout the several views.

FIG. 1 is an elevational view of the helical balloon catheter of the present invention as disposed and inflated in a blood vessel which is depicted in cross-section.

FIG. 2 is an schematic elevational view of the helical balloon catheter of the present invention.

FIG. 3 is a cross-sectional view of the helical balloon catheter of the present invention taken along section line A—A of FIG. 2.

FIG. 4 is a cross-sectional view of the helical balloon catheter of the present invention taken along section line B—B of FIG. 2.

FIG. 5 is a cross-sectional view of the helical balloon catheter of the present invention taken along section line C—C of FIG. 2.

FIG. 6 is a cross-sectional view of the helical balloon catheter of the present invention taken along section Line D—D of FIG. 1.

DETAILED DESCRIPTION OF THE PREFERRED EMBODIMENT

Figure 7:
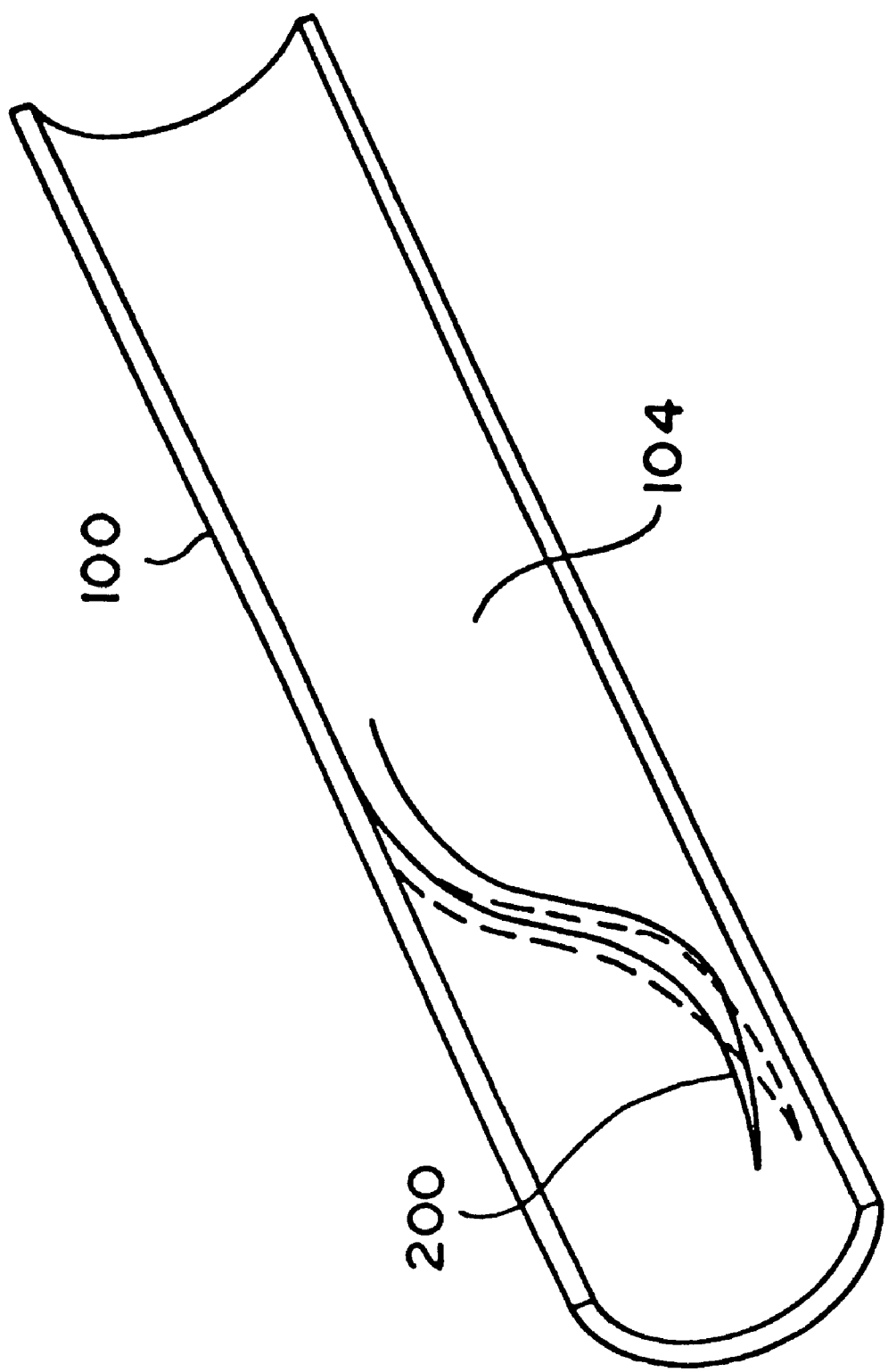
FIG. 7 is a perspective cutaway view of a blood vessel schematically illustrating a spiral or helical dissection formed therein.

The present invention is an improvement to the device disclosed and illustrated in U.S. Pat. No. 5,383,856, issued to the same inventor, and that patent is hereby incorporated by reference, in its entirety. The following description of FIGS. 1–7 is essentially identical to that set forth in the aforenoted patent, and is followed by a description of the unique features of the instant invention.

Referring initially to FIGS. 1 and 2, the multiple helical balloon catheter is designated by numeral 10. Catheter 10 has a central support tube defining a central lumen 12 adapted to carry therein a guide or advance wire 14 which, as is generally known in the art, is used to facilitate insertion of the catheter to the desired position within the blood vessel. In the present invention, because the device will be used primarily for repair of dissections in blood vessels, the desired position for the catheter in the blood vessel will ordinarily be at the site where the dissection has occurred and/or has been detected.

Disposed at the outer surface of the central lumen 12, and extending therealong in a longitudinal direction, are a plurality of balloon elements 16. The depicted preferred embodiment employs two such balloon elements. The balloon elements 16 are preferably disposed near a distal end 18 of the catheter. The balloon elements 16 are also preferably arranged in a "double helix", wherein two diametrically opposed spiraling or helical balloon elements wind around the central support tube and lumen 12. The balloon elements 16 are preferably bonded to the outer surface of the central lumen with a suitable cement or adhesive 20 (see FIG. 5), along the entire longitudinal extent of the elements, in order to maintain the double helical orientation and positioning with respect to the central lumen throughout the insertion and repair procedure. This bonding can be continuous along the longitudinal extent or the adhesive 20 can be applied at substantially regular intervals along the longitudinal extent.

FIGS. 2–5 illustrate preferred constructional features of the double (two balloon segments) helical balloon catheter 10 in one of the preferred embodiments of the present invention. As can be seen in FIG. 2, the central lumen 12 is preferably fluidically isolated from the balloon elements 16 and the means for inflating or expanding the balloon elements. At a proximal end 19 of the balloon subassembly 22, a fluid supply sleeve 24, also referred to as an inflation port, surrounds the central lumen and is coupled to the balloon elements 16 in a fluid-tight connection. The fluid supply sleeve 24 is shown as being coextensive and concentric with the central support tube or lumen 12 and the sleeve extends to the outside of the body. It should be recognized that the fluid supply sleeve (inflation port) and central support tube or lumen 12 can be arranged in many other preferred constructions, one further example of which is an approximately crescent-shaped inflation port extending along the central support tube, wherein the inner portion of the inflating port is integral with, or conforms to and is contact with, the outer surface of the central support tube. The inflating fluid, generally a solution of saline and a contrast agent, is supplied to the balloon elements through this sleeve 24.

The proximal ends of balloon elements 16 are fluidly coupled to and extend toward a distal end of the catheter from the fluid supply sleeve 24. The sleeve acts generally in the nature of an inextensible (under the range of fluid pressures experienced in this service) collar. As can be seen in FIG. 3, the proximal end of each of the balloon elements 16 occupies substantially one-half of the area between central lumen 16 and sleeve 24. When the inflating fluid is transmitted to sleeve 24, the flow of fluid is thus essentially evenly divided into each of the two balloon elements 16. It may be preferred, from a manufacturing standpoint, to produce the sleeve 24 and the balloon elements 16 as an integral unit in an extrusion process.

The balloon elements 16 extend from the fluid supply sleeve 24 in diametrically opposed helical paths toward the distal end of catheter 10. It is to be noted, that, for ease of illustration, the balloon elements 16 in FIG. 2 are shown as not being bonded to the central support tube 12, however, as previously noted, these elements 16 are required to be bonded to the central member, at least at intermittent points along their extent.

At a distal end of the balloon elements 16, the ends 28, 30 of the elements are sealed down against the outer surface of the support tube or central lumen 12 (FIGS. 2, 4) to ensure that the inflating fluid transmitted into the balloon elements is retained therein to expand or inflate the balloons.

Other means of attaching the balloon elements to the catheter and for supplying fluid into the elements will be readily envisioned by those skilled in the balloon catheter art. FIG. 1, for example, depicts a variation on the construction illustrated in FIGS. 2–5. In FIG. 1, the central support tube or lumen 12 is provided with a fluid supply tube 40 which does not terminate at the proximal end of the balloon elements, as does sleeve 24 in FIG. 2, but further extends concentrically around and along the central lumen for a distance somewhat greater than the longitudinal extent of the balloon elements 16. Supply tube 40 is sealed against the central lumen 12 at its distal end 42, and is coupled at its proximal end 44 to a fluid supply conduit 46 which extends concentrically with along central lumen 12 to a point outside the patient's body, where it is coupled to means for supplying fluid to inflate the balloon elements 16. This fluid supply conduit 46 operates much in the same manner as does sleeve 24 in the FIG. 2 embodiment.

Supply tube 40 has bonded thereto the two balloon elements 16, with the open proximal and distal ends of the balloon elements being connected in a fluid-tight manner to tube 40. Tube 40 is provided with fluid openings 48 at its proximal and distal ends which place the tube 40 in fluid communication with the proximal and distal ends of balloon elements 16. Fluid delivered through conduit 46 enters tube 40 and passes through openings 48 to inflate the balloon elements to the desired pressure. It is to be noted that, in this alternative preferred embodiment, the supply tube 40 is substantially inextensible as compared with the balloon elements 16, such that the inflating fluid supplied inflates the balloon-elements without substantially inflating or expanding the diameter of the tube 40. As with the FIG. 2 embodiment, it may be preferred to form the entire FIG. 1 structure as an integral unit in an extrusion process.

FIG. 5 illustrates, in somewhat schematic form, the cross-section of double helical balloon catheter shown in FIG. 1. The balloon elements 16 are shown in solid lines in their inflated or expanded condition, and are shown in broken lines in their unexpanded condition. The inner wall of the blood vessel is schematically represented by circle 104 in FIG. 5. It can be seen that, at any given point along the longitudinal extent of the balloon elements, a path for the flow of blood through the blood vessel undergoing repair is provided around the outer surfaces of the central support tube or lumen 12, and the expanded or inflated balloon elements 16. The cross-section shown in FIG. 6 is essentially the same as that of FIG. 5, with the exception that the concentric arrangement of the central support tube or lumen 12 and fluid supply tube 40 can be seen in FIG. 6, with the balloon elements being bonded to the outer tube 40.

The use and operation of the double helical balloon catheter device as a blood vessel repair tool will now be described with reference to all figures, but in particular FIGS. 1 and 7. As shown in FIG. 1, the balloon elements 16 are in position and are expanded or inflated, which brings the outer surfaces thereof into contact with the inner wall 104 of the blood vessel 100. It will be readily understood to those of ordinary skill in this field of art that when the catheter is being inserted through the blood vessel to its desired position, the balloon elements 16 will not be inflated (see broken lines, FIG. 5) and the catheter can thus be inserted through the blood vessel without any substantial and potentially damaging scraping or rubbing of the balloons against the walls of the blood vessel. In this respect, techniques for inserting dilatation balloon catheters as have been previously disclosed in the art will generally be applicable to the insertion of the balloon catheter of the present invention, and no detailed discussion of such techniques thus will be included herein.

FIG. 1 illustrates that the balloon catheter 10 of the present invention provides a relatively open blood flow path down the main trunk or blood vessel 100, wherein the blood flowing past the balloon catheter 10 moves through the two approximately helically extending cavities 102 created by the outer surfaces of the balloon elements 16 and central lumen 12, and bordered by the inner wall 104 of the blood vessel 100 (see also FIG. 5).

The method for repairing a dissection at an inner wall of a blood vessel with the device of the present invention involves inserting the catheter 10 into the cardiovascular system of a patient to be treated, with the balloon elements 16 being in their unexpanded or uninflated condition. The distal end of the catheter with guide wire 14 protruding therefrom is first inserted, and the catheter is advanced within the cardiovascular system until the balloon elements are situated in the region within the blood vessel to be repaired where the dissection has been detected. The catheter is then oriented, by rotating the catheter as necessary, such that one of the two balloon elements is positioned immediately adjacent to, but not necessarily touching, the dissection to be repaired. At this point, the balloon elements 16 are expanded or inflated to bring the outer or bearing surface 17 of the balloon element 16 adjacent the dissection into intimate contact with the dissection, which also will bring the outer balloon into contact with the wall of the blood vessel at a point substantially diametrically opposite the dissection. The applied pressure is thus focused n the flat 200 (FIG. 7) formed by the dissection, urging the flap 100 back into the vessel wall from which it has become detached.

With the balloon elements thus inflated, blood is permitted to continue flowing past the balloon elements 16 along the main trunk, and into unobstructed side branches in the area at which the balloon elements are disposed. The balloons are left in their inflated or expanded condition for a length of time, most likely on the order of tends of minutes to several hours, which is estimated in advance to be sufficiently long to obtain a substantially permanent tacking of the flap against the inner wall 104 of the blood vessel 100. After that time period has elapsed, the balloon elements are brought back to their uninflated or unexpanded state, and the catheter may then be withdrawn.

It will be readily apparent that various diagnoses may be made with respect to determining whether the tacking of the dissection flap 200 has been successfully accomplished prior to the removal of the catheter, and it is expected that such diagnostic procedures will be so employed.

FIG. 7 illustrates flap 200 resulting from the dissection in the blood vessel wall. The dissection commonly appears in an approximately helical pattern, as is shown. The balloon catheter of the present invention thus is very well suited to repair such dissections, as the helically extending balloon elements 16 can be positioned such that pressure is brought to bear against the flap 200 along most, if not all, of its entire length.

By providing an open helical path for blood to flow along the blood vessel under repair, the device permits the use of balloons which extend along a greater length L (FIG. 2) than the balloons employed on prior dilatation catheters. The preferred length L of the balloons on the present device is on the order of 40 centimeters, as compared with a 10–20 centimeter balloon length in existing commercial dilatation catheters. As can be seen in referring back to FIG. 1, the design of the helical balloon catheter of the present invention preserves blood flow to side branches 106 extending off of the blood vessel under repair, even though the balloons are of a greater length than those previously employed in dilatation catheters.

Other variations on the illustrated preferred embodiments are possible. The balloon elements 16 as shown have a round cross-sectional shape, however, other shapes, such as triangles, may be employed as well. A preferred material of construction for the catheter of the present invention is high density polyethylene, although other materials may be suitable for use. The construction of the device can be modified, if desired, to provide the capability to independently inflate each balloon element. Lastly, while the catheter 10 is shown in the preferred embodiments as having two diametrically opposed balloon elements 16 extending in a helical pattern, it may be possible to employ three or more helically-extending balloon elements which are spaced equidistantly around the central support tube 12.

Since the issuance of U.S. Pat. No. 5,383,856, to the instant inventor, it has further been determined that a balloon catheter having a central support tube and a plurality of balloon elements extending helically around the central tube, as shown in FIGS. 1–7 herein, can advantageously be used in medical procedures in which the treatment or therapy is to be administered by holding a therapeutic agent in a central portion of a blood vessel for a predetermined period of time. The catheter device for administering therapy from within a blood vessel preferably will have diametrically opposed forces, or forces applied at substantially equal distances around the periphery of a cross-section of the blood vessel, and will, at the same time, permit blood to flow past the balloons, even when inflated.

One type of therapy that is currently being explored is a radiation therapy in which the object is to center, in an artery or other blood vessel, a radium implant, for periods of time on the order of fifteen minutes. For such radiation treatment, it is important to position the radium implant as closely as possible to the center of the artery. It is also important that blood flow past the implant be maintained, so as to not further disrupt normal body functions. The multiple helical balloon catheter 10, when the balloons are inflated, very effectively centrally positions the central support tube or central lumen 12 in the blood vessel at the region where the balloons 16 are located. As noted previously, the use of two or more equally spaced balloons 16 allows blood to flow axially past the balloons, as would be recognized in viewing FIGS. 1 and 6, for example.

In using the multiple helical balloon catheter in a radiation therapy procedure, the method for inserting the catheter and inflating the balloons would be essentially identical to the steps used in the method for repairing blood vessel dissections. The catheter 10 is inserted to a position at which balloon elements 16 are at the position along the extent of the artery or other blood vessel where the radium implant will later be placed in the artery, and the balloon elements are then inflated such that the balloon elements exert force against the wall of the artery at equidistant points around the circumference of the artery. In this method, since there is generally no dissection being repaired, there is no need to further position the catheter such that one of the balloons will be inflated into contact with such a dissection.

Once the balloon elements have been inflated, a radiation source selected for use in this radiation therapy, generally a radium implant 300 (shown schematically in FIG. 1), is delivered through central lumen 12 to a position within central lumen 12 around which balloon elements 16 are positioned, and the radium implant 300 is maintained at that location for the prescribed period of time, commonly about fifteen (15) minutes. During that time, balloon elements 16 are continuously maintained in their inflated condition to maintain the central lumen 14 at the center of the blood vessel 100, while also permitting blood to flow past the balloons.

Upon completion of the treatment or therapy, the radium implant 300 may be withdrawn, and the balloons may then be deflated and the catheter withdrawn from the blood vessel. The insertion and retraction of the radium implant may be done using a guide wire or any device currently employed in the art for advancing objects through catheters inserted in blood vessels.

Figure 8:
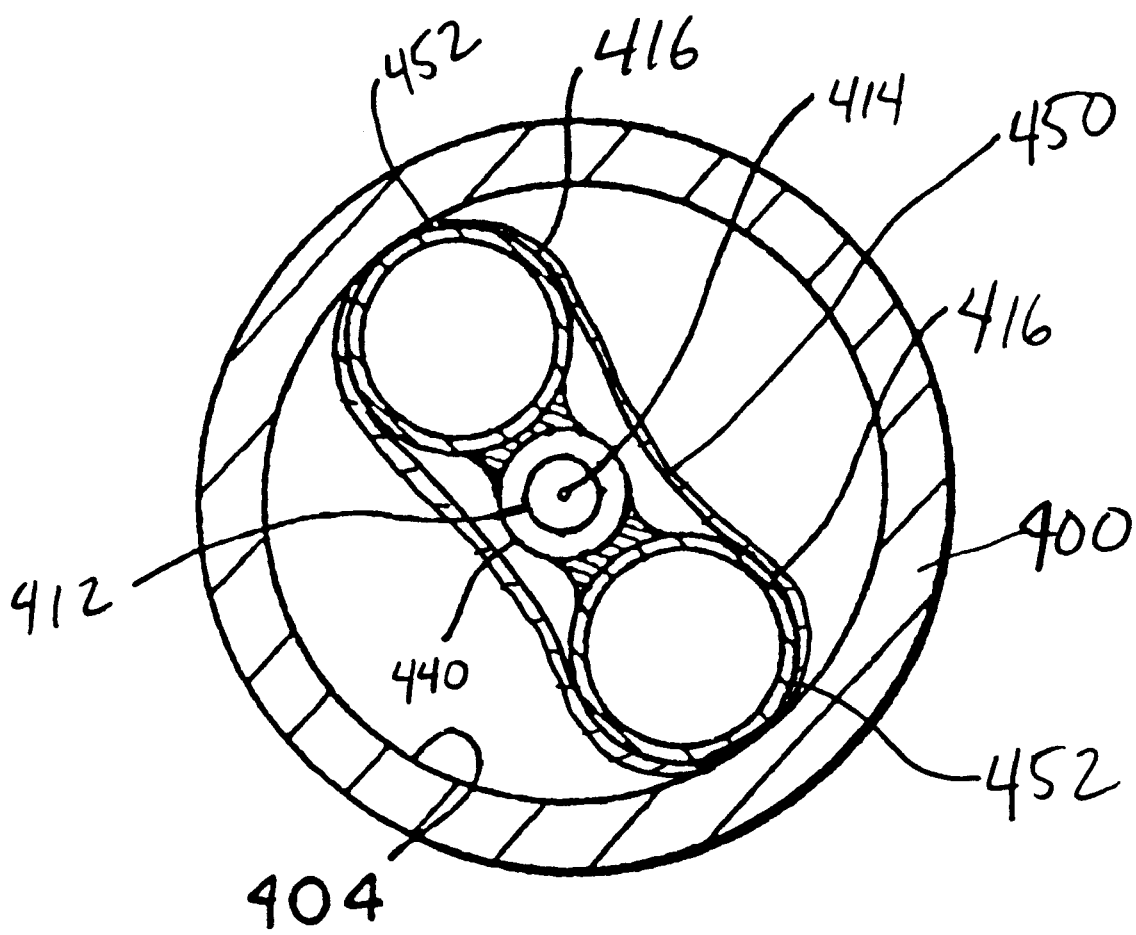
FIG. 8 is a cross-sectional view of a helical balloon catheter in an alternative embodiment of the present invention, in which the catheter is not used to repair a blood vessel dissection, but instead is used to center a central support tube in the blood vessel for use in various medical treatment processes.

An alternative preferred embodiment of the multiple helical balloon catheter shown in FIGS. 1–7 is depicted in the cross-sectional view of FIG. 8. In the FIG. 8 embodiment, it is seen that the equidistantly-spaced balloons 416, the inflation tube 440, and the central lumen 412 of the catheter 400 are surrounded by flexible membrane 450. The thin membrane 450 is secured to at least the radially outer portions 452 of the balloon elements 416, and, when the balloon elements 416 are in their uninflated or collapsed condition, the membrane 450 collapses with the balloons.

The membrane 450 preferably extends or wraps around the entire catheter assembly 400 along the entire area where external balloon elements 416 are disposed. The membrane 450 aids in maintaining the desired equidistant spacing of the balloon elements 416 when the balloon elements are inflated to engage the wall 404 of the blood vessel 400, and reinforces the overall structural integrity of the device when inflated. The membrane may further serve to facilitate blood flow past the inflated balloon section, in that the more uniform surfaces which the blood flow comes into contact with may induce less turbulence.

The thin membrane 450 may preferably be made of the same or a similar material as those used in the art for balloons of balloon catheters. The membrane is, however, preferably thinner than the wall thickness of the balloons. For example, the membrane may be made of polyethylene, polyethylene terepthalate (PET), nylon, or a polyolefin copolymer. The membrane 450 may be secured to the balloon elements 416 by a suitable adhesive, or may preferably be fused or joined thereto in an extrusion process.

It is to be noted that, while the specific example of a method for conducting radiation therapy using the catheter of the present invention is presented herein, the method is more broadly applicable to other forms of therapeutic use in which a treatment source is required to be positioned at a centered position within a blood vessel. The device and method may be used in conducting gene therapy, providing highly localized drug delivery, and positioning any suitable biologically active agent in a blood vessel for treatment or therapy. Various therapeutic or biological agents would, in such methods, be used in place of the radium implant described above in the radiation therapy treatment process.

The foregoing description is provided for illustrative purposes only, and variations and modifications to the depicted and described preferred embodiments may become readily apparent to those of ordinary skill in the art without departing from the spirit and scope of the present invention. Accordingly, the scope of the invention is to be determined by reference to the appended claims.

What is claimed is:

1. A method for providing medical treatment from within a blood vessel of a patient comprising the steps of:

(a) providing a catheter comprising an elongated support tube having distal and proximal ends, said support tube defining a central lumen, said catheter further having a radially expandable balloon means carried by and integrally connected to said support tube at a predetermined point between the proximal end and the distal end thereof, and means for expanding and contracting said balloon means, said balloon means comprising at least two spiral-shaped balloon elements extending helically around said support tube along a predetermined length of said support tube, said at least two balloon elements being spaced equidistantly around said support tube, and a flexible membrane surrounding said balloon means and said support tube, said flexible membrane being secured to and closely conforming to outer surfaces of said balloon elements whereby said membrane moves to an expanded position when said balloon means is expanded, and moves to a contracted position when said balloon means is contracted, (b) inserting said distal end of said catheter into a cardiovascular system of the patient with said balloon means in an unexpanded condition;

(c) advancing said catheter within the cardiovascular system until said balloon means is situated in the blood vessel at a region where said medical treatment is to be administered;

(d) centering said portion of said support tube having said balloon elements disposed thereon by expanding said balloon means to bring said at least two balloon elements into intimate contact with an inner wall of the blood vessel, while permitting blood to flow past the balloon means through open paths left between said balloon element, and permitting blood to flow to unobstructed side branches of blood vessels in the region in which the balloon means is disposed;

(e) retaining said balloon elements in said expanded condition;

(f) inserting a treatment agent through said support tube to a treatment position at which said expanded balloon elements are located, and maintaining said treatment agent at the treatment position for a predetermined period of time;

(g) withdrawing said treatment agent from the treatment position;

(h) contracting the balloon means; and (i) withdrawing said catheter from the body of the patient.

2. The method as set forth in claim 1, wherein said balloon means comprises only two balloon elements, and said two balloon elements extend in diametrically opposed helical paths along said support tube.

3. The method as set forth in claim 1, wherein said treatment agent is a radiation therapy treatment agent.

4. The method as set forth in claim 1, wherein said treatment agent is a biologically active agent.

5. A method for providing medical treatment from within a blood vessel of a patient comprising the steps of:

(a) providing a catheter comprising an elongated support tube having distal and proximal ends, said support tube defining a central lumen, said catheter further having a radially expandable balloon means carried by and integrally connected to said support tube at a predetermined point between the proximal end and the distal end thereof, and means for expanding and contracting said balloon means, said balloon means comprising at least two spiral-shaped balloon elements extending helically around said support tube along a predetermined length of said support tube, said at least two balloon elements being spaced equidistantly around said support tube, (b) inserting said distal end of said catheter into a cardiovascular system of the patient with said balloon means in an unexpanded condition;

(c) advancing said catheter within the cardiovascular system until said balloon means is situated in the blood vessel at a region where said medical treatment is to be administered;

(d) centering said portion of said support tube having said balloon elements disposed thereon by expanding said balloon means to bring said at least two balloon elements into intimate contact with an inner wall of the blood vessel, while permitting blood to flow past the balloon means through open paths left between said balloon element, and permitting blood to flow to unobstructed side branches of blood vessels in the region in which the balloon means is disposed:

(e) retaining said balloon elements in said expanded condition;

(f) inserting a radiation therapy treatment agent through said support tube to a treatment position at which said expanded balloon elements are located, and maintaining said radiation therapy treatment agent at the treatment position for a predetermined period of time;

(g) withdrawing said radiation therapy treatment agent from the treatment position;

(h) contracting the balloon means; and (i) withdrawing said catheter from the body of the patient.

6. A method for providing medical treatment from within a blood vessel of a patient comprising the steps of:

(a) providing a catheter comprising an elongated support tube having distal and proximal ends, said support tube defining a central lumen, said catheter further having a radially expandable balloon means carried by and integrally connected to said support tube at a predetermined point between the proximal end and the distal end thereof, and means for expanding and contracting said balloon means, said balloon means comprising at least two spiral-shaped balloon elements extending helically around said support tube along a predetermined length of said support tube, said at least two balloon elements being spaced equidistantly around said support tube, (b) inserting said distal end of said catheter into a cardiovascular system of the patient with said balloon means in an unexpanded condition;

(c) advancing said catheter within the cardiovascular system until said balloon means is situated in the blood vessel at a region where said medical treatment is to be administered;

(d) centering said portion of said support tube having said balloon elements disposed thereon by expanding said balloon means to bring said at least two balloon elements into intimate contact with an inner wall of the blood vessel, while permitting blood to flow past the balloon means through open paths left between said balloon element, and permitting blood to flow to unobstructed side branches of blood vessels in the region in which the balloon means is disposed;

(e) retaining said balloon elements in said expanded condition;

(f) inserting a biologically active treatment agent through said support tube to a treatment position at which said expanded balloon elements are located, and maintaining said biologically active treatment agent at the treatment position for a predetermined period of time;

(g) withdrawing said biologically active treatment agent from the treatment position;

(h) contracting the balloon means; and (i) withdrawing said catheter from the body of the patient.

7. A balloon catheter comprising:

a central support tube;

means for centering a portion of said central support tube within a blood vessel, said centering means comprising a plurality of balloon elements disposed at a predetermined point between a proximal end and a distal end of said central support tube;

each of said plurality of balloon elements having a longitudinal extent, each of said plurality of balloon elements winding around said central support tube in a helical pattern, wherein said plurality of balloon elements are spaced equidistantly around a circumference of said central support tube; and means fluidly coupled to said balloon elements for expanding said balloon elements into contact with an inner wall of a blood vessel of a patient when said catheter and said balloon elements are in a desired position within the blood vessel to center said central support tube within the blood vessel;

means for returning said balloons to an unexpanded condition;

means for administering treatment disposed within said central support tube; and wherein said balloon catheter further comprises a flexible membrane extending around said plurality of balloon elements and said central support tube, said flexible membrane being secured to and closely conforming with outer portions of said balloon elements that are brought into contact with said blood vessel inner wall.

8. A balloon catheter as recited in claim 7, wherein said flexible membrane and said balloon elements form a coextruded structure.

9. A balloon catheter as recited in claim 7, wherein each of said plurality of balloon elements is bonded to said central support tube along substantially an entire length of said balloon.

10. A balloon catheter as recited in claim 7, further comprising a guide wire removably housed within said central support tube.

11. A balloon catheter as recited in claim 7, wherein said means for administering treatment comprises a biologically active agent positioned in said central support tube.

12. A balloon catheter as recited in claim 7, wherein said means for administering treatment comprises a radiation therapy agent positioned in said central support tube.

* * * * *